United States Patent [19]

Dahners

[11] Patent Number: 5,162,039
[45] Date of Patent: Nov. 10, 1992

[54] DISTRACTION AND REDUCTION DEVICE

[76] Inventor: Laurence E. Dahners, 102 Azalea Pl., Chapel Hill, N.C. 27514

[21] Appl. No.: 822,674

[22] Filed: Jan. 21, 1992

[51] Int. Cl.⁵ .............................................. A61F 5/00
[52] U.S. Cl. ...................................... 602/23; 602/32; 602/36
[58] Field of Search ............... 602/38, 32, 19, 5, 23, 602/24, 27, 36, 37; 606/54, 55, 57, 58, 105

[56] References Cited

U.S. PATENT DOCUMENTS

| | | | |
|---|---|---|---|
| 1,238,224 | 8/1917 | Vickers | 602/23 |
| 1,880,945 | 10/1932 | Ettinger | 602/23 |
| 1,967,471 | 7/1934 | Ettinger | 602/37 |
| 1,982,140 | 11/1934 | Martin | 602/37 |
| 2,024,325 | 12/1935 | Allen | 602/23 |
| 3,454,002 | 7/1969 | Westlake | 602/23 |
| 3,756,227 | 9/1973 | Sager | 602/23 |
| 4,336,796 | 6/1982 | Andrews | 602/23 |
| 4,407,277 | 10/1983 | Ellison | 5/648 |
| 4,584,995 | 4/1986 | Koenemen | 606/54 |
| 4,608,971 | 9/1986 | Borschneck | 602/23 |

*Primary Examiner*—Michael A. Brown
*Attorney, Agent, or Firm*—Rhodes, Coats & Bennett

[57] ABSTRACT

A distraction and reduction device includes a main support bar having a saddle at one end thereof for engagement with the patient's groin or axilla. A support arm is mounted on the support bar and supports a force applying unit. The force applying unit is connected to a means for engaging the body and applies a distally directed force to the patient's limb to distract the bone fragments. As distraction force is being applied to the fractured limb, the saddle presses into the patient's groin or axilla thereby providing resistance against the traction force. The invention also includes a fracture reducing unit which is used to selectively apply pressure to the limb at the location of the fracture to correct any misalignment of the bone fragments.

20 Claims, 4 Drawing Sheets

DISTRACTION AND REDUCTION DEVICE

FIELD OF THE INVENTION

The present invention relates generally to surgical devices and more particularly to an apparatus for reducing fractures of the long bones.

BACKGROUND OF THE INVENTION

It is essential that fractures of the long bones be properly aligned prior to internal fixation by an intramedullary nail. Methods used to obtain reduction of the fracture include positioning of the patient, manual manipulation by the surgeon, traction, or a combination of these methods. Since these methods do not always result in proper anatomical alignment of the bone fragments, numerous devices have been developed to assist surgeons.

For example, U.S. Pat. No. 4,929,247 discloses a bone compression and distraction device for distracting the ends of the bone fragments. The device includes two blocks which are seated on the ends of a splint and are secured to respective bone fragments by bone screws. The blocks are joined together by a pair of threaded rods which permit the blocks to be pulled together or pushed apart to compress or distract the ends of the bone. Once the bone ends are properly positioned, the splint is fixed to the bone and the blocks are removed.

U.S. Pat. No. 5,003,969 discloses a device for correcting lateral, posterior, or anterior displacement of the bone ends. The device includes a plurality of spanning bars which are disposed around the patient's limb at the location of the fracture. Each spanning bar includes two pressure pads having threaded shafts engaged with the spanning bars. A knob on the threaded shaft enables the surgeon to control the pressure applied to the limb by rotating the knob.

Other devices known to applicant include U.S. Pat. No. 4,978,348 which discloses a compression and distraction device, and U.S. Pat. Nos. 2,024,325; 4,271,832; and 4,475,546 which disclose various types of leg splints.

SUMMARY AND OBJECTS OF THE INVENTION

The present invention is a device to assist surgeons in distracting and reducing fractures, particularly fractures of the femur and humerus. The device consists of an elongated bar which is disposed parallel to the fractured limb. At one end of the bar there is a saddle adapted to fit into the patient's groin or axilla. A force-applying unit is slidably mounted on the bar and includes means for applying a distally directed force to the fractured limb. The force applying unit engages with a means for engaging the body such as a Kirschner-type wire bow, which applies the traction force to the injured limb. As the traction force is applied, the saddle is pressed into the groin or axilla and the ends of the fractured bone are pulled apart. For fractures of the tibia and forearm, similar force applying wires and means for engaging the body can be attached to both ends of the bar (rather than a saddle at one end).

The invention also includes a reducing unit for correcting any lateral, posterior, or anterior displacement of the bone ends. The reducing unit includes two generally C-shaped pressure applicators for applying pressure to the fractured limb. The amount and direction of the pressure is controlled by the surgeon to obtain alignment of the bone ends.

It is therefore an object of the present invention to provide a fracture alignment device for reducing and distracting fractures of the long bones.

Another object of the present invention is to provide a fracture alignment device which is sterilizable.

Another object of the present invention is to provide a fracture alignment device which is relatively simple in construction and easy to use.

Still another object of the present invention is to provide a fracture alignment device which is lightweight, portable, and easily disassembled.

Another object of the present invention is to provide a fracture alignment device which will not interfere with fluoroscopic imaging.

Other objects and advantages of the present invention will become apparent and obvious from a study of the following description and the accompanying drawings which are merely illustrative of such invention.

DETAILED DESCRIPTION OF THE INVENTION

Figure 1:
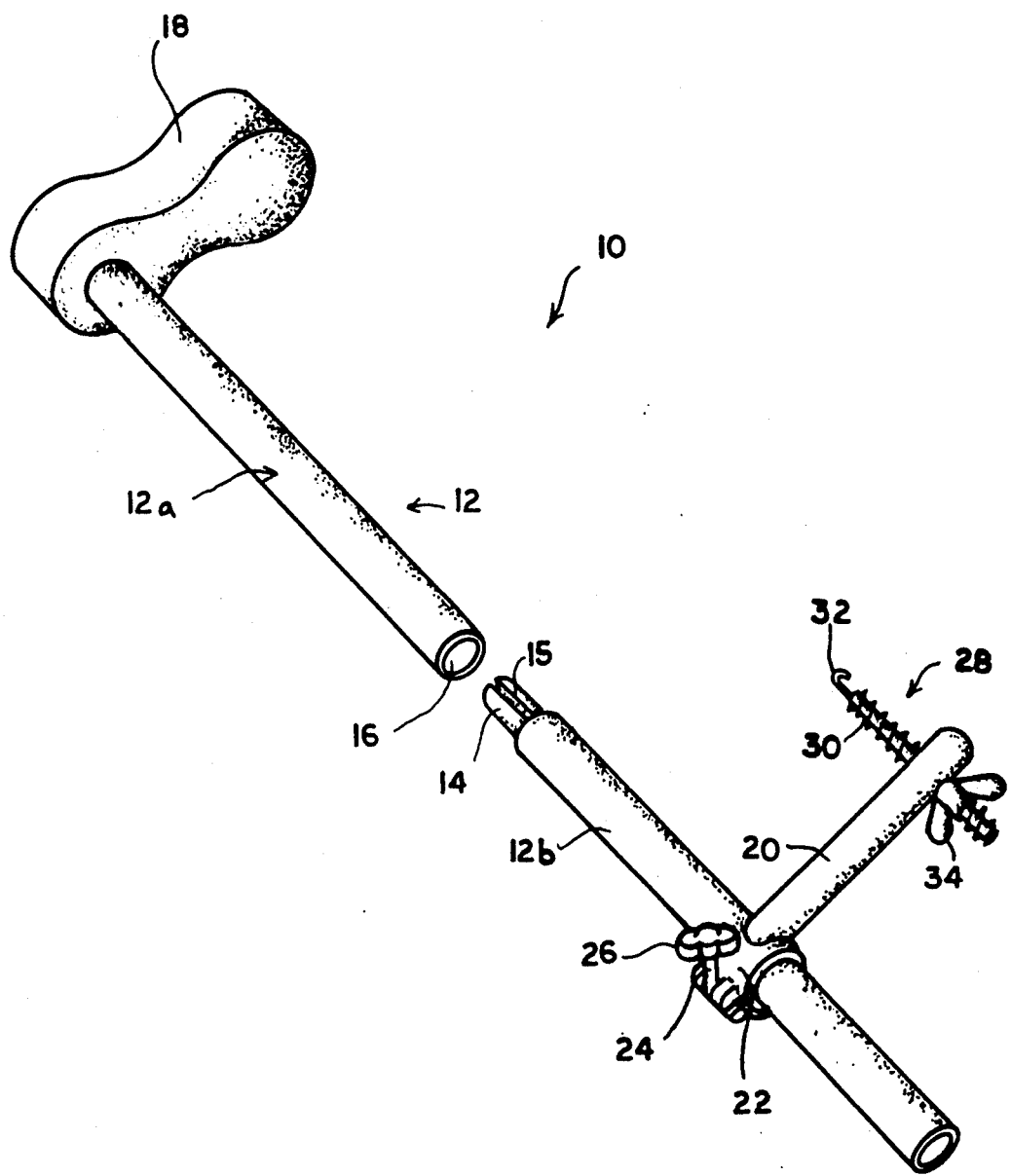
FIG. 1 is a perspective view of the distraction device of the present invention.

Referring now to the drawings, the distraction and reduction device of the present invention is shown therein and indicated generally by the numeral 10. The distraction and reduction device 10 provides means for correcting limb length and for reducing lateral, anterior, or posterior displacement of the bone fragments.

The distraction and reduction device 10 includes a main support bar 12 made preferably of a radiolucent material, such as epoxy fiberglass, so as not to interfere with fluoroscopic imaging. The main support bar 12 comprises two separable bar segments, 12a and 12b, which can be disassembled easily for sterilization in an autoclave. The lower bar segment 12b includes an end piece 14 which inserts into the open end of the upper bar segment 12a. In this design, the end piece 14 is formed with a keyway 15 which cooperates with a key (not shown) on the inner surface of the upper post segment 12a to prevent the segments from rotating relative to one another, but other means may be used to prevent rotation.

Rigidly fixed to the upper segment 12a is a saddle 18. The saddle 18 is designed to fit into the patient's groin, or into the patient's axilla in the case of a broken arm. The support bar 12 attaches to the saddle 18 at one end so that when the saddle 18 is fitted into the patient's groin, the support bar 12 extends along the anterior surface of the fractured limb. The function of the saddle is to provide resistance while traction is being applied to the broken limb. For the patient's comfort, it is preferred that the saddle 18 be padded.

A support arm 20 extends perpendicularly from the main k support bar 12. The support arm 20 includes a bar clamp 22 at one end for clamping the support arm 20 into the main support bar 12. The bar clamp 22 includes two halves which are joined by a hinge (not shown). A swing bolt 24 having a large knob 26 secures the two halves around the main support bar 12. This type of bar clamp 22 is widely used in traction devices and is well known to those skilled in the art, but other types of attachments to the main support bar may be used.

A force applying unit 28 is secured to the outer end of the support arm 20. The force applying unit 28 is used to apply a distally directed force to the fractured limb to correct limb length. In the disclosed embodiment, the force applying unit 28 includes a threaded rod 30 having a hook 32 at one end. The threaded rod 30 extends through the support arm 20 and has a wing nut 34 threaded thereon. By turning the wing nut 34, the threaded rod 30 is moved axially back and forth parallel to the main support bar 12. Other types of mechanical devices might also be used to apply force.

Figure 5:
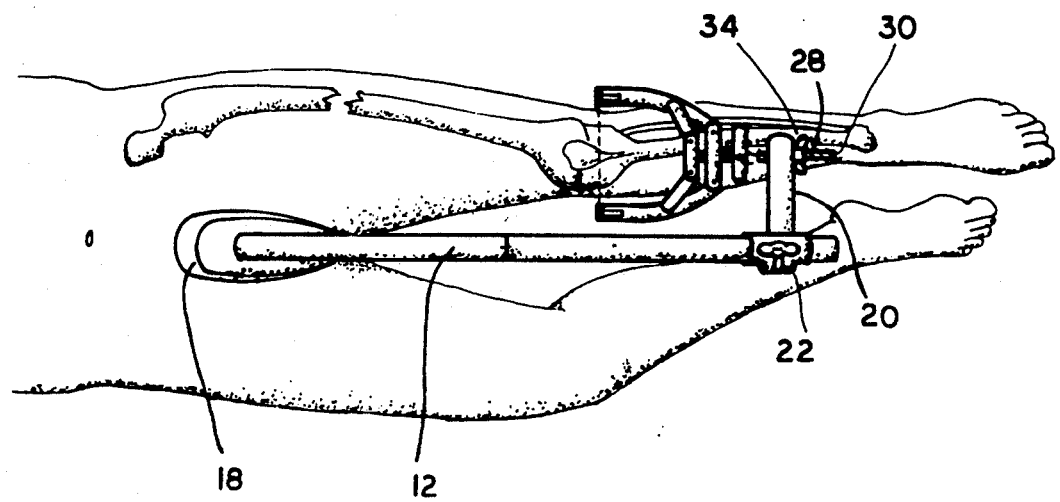
FIG. 5 is a perspective view illustrating the use of the distraction device to distract a bone fracture.
Figure 6:
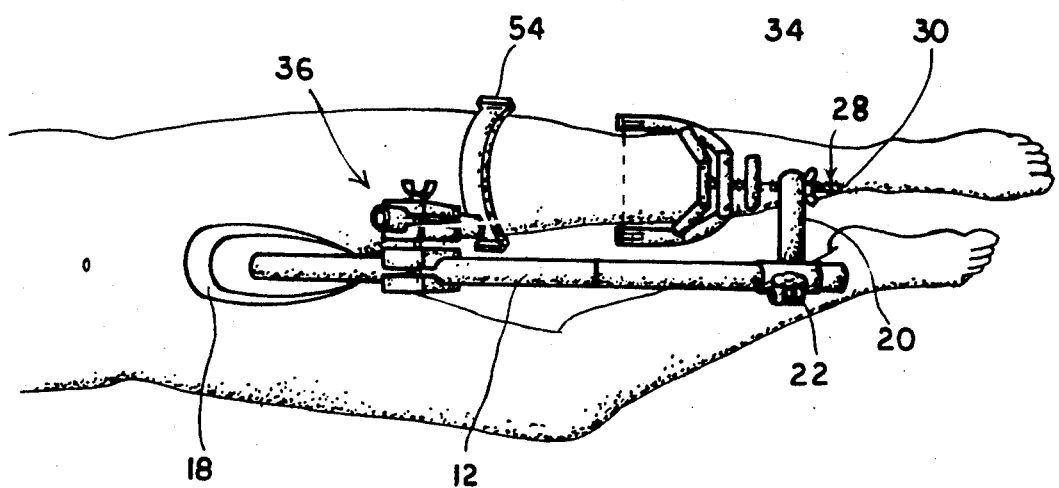
FIG. 6 is a perspective view illustrating the use of the distraction device to distract and reduce a bone fracture.

The force applying unit 28 is adapted to engage with various conventional body engaging means, such as a Kirschner-type wire bow. More particularly, the wire bow or other means for engaging the body engages with the hook 32 of the force applying unit 28, as shown in FIGS. 5 and 6. Thus, the axial movement of the threaded rod 30 imparts a traction force to the fractured limb through the body engaging means. This traction force tends to pull the fractured ends of the bone apart.

Although a Kirschner-type wire bow is used in the disclosed embodiment, there are numerous other devices that could also be employed. Such other devices include, without limitation, a Steinman pin, and external devices such as straps or boots.

Figure 2:
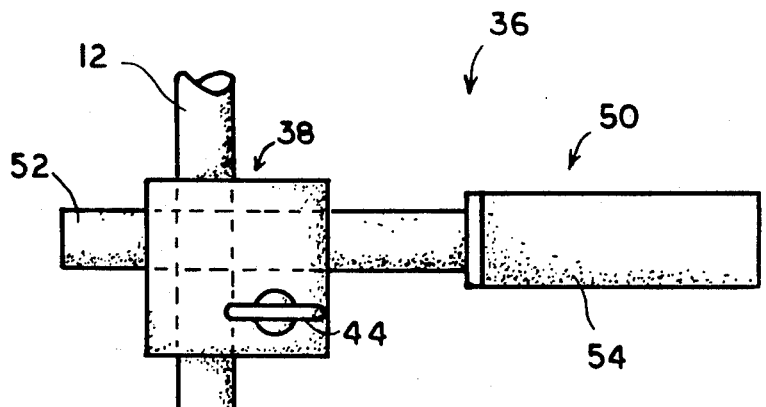
FIG. 2 is a top plan view of the reduction unit which forms a part of the invention.
Figure 3:
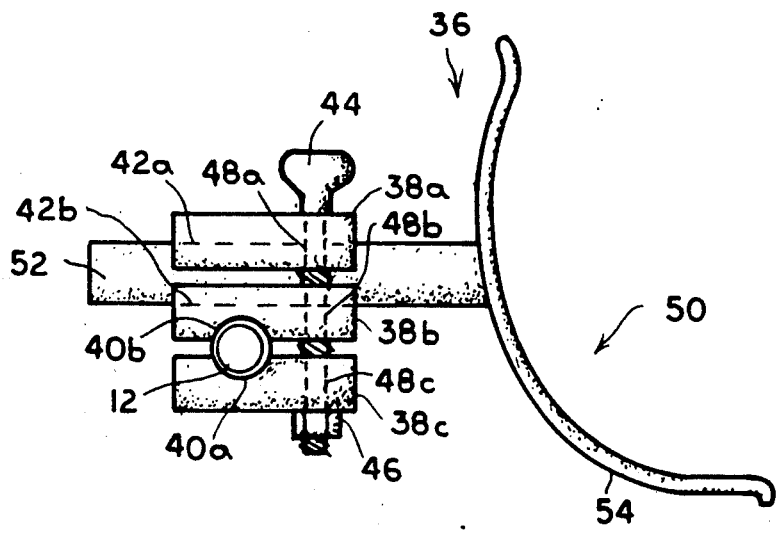
FIG. 3 is an elevational view of the reduction unit.
Figure 4:
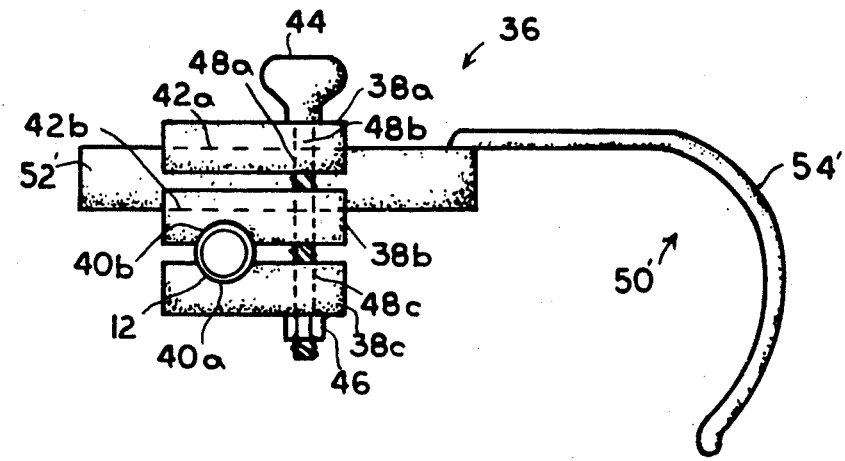
FIG. 4 is an elevational view of the same reduction unit showing an alternate embodiment of the pressure applicator.

Referring now to FIGS. 2–4, the reduction unit 36 of the present invention is shown. The reduction unit 36 is used when needed to correct medial, lateral, anterior, or posterior displacement of the bone ends. The reduction unit 36 includes a mounting block indicated generally at 38, and a pressure applicator indicated generally at 50. The mounting block 38 is used to mount the pressure applicator 50 to the support bar 12, and also to provide for translational and rotational movement of the pressure applicator 50.

The mounting block 38 includes three block segments- an upper block segment 38a; a middle block segment 38b; and a lower block segment 38c. All three block segments include aligned bolt holes 48a, 48b, and 48c. The block segments are held together by a long wing bolt 44 which extends through the aligned holes in the individual block segments and which is secured by a nut 46. Two of the block segments form a clamp to engage the support bar 12. The lower surface of the middle block segment 38c and the upper surface of the lower block segment 38b are formed with semi-circular grooves 40a and 40b for receiving the main support bar 12 of the distraction device 10. Similarly, the middle and upper block segments 38b and 38c form a clamp for engaging the shaft 52 of the pressure applicator 50 to be hereinafter described. The upper surface of the middle block segment 38b and the lower surface of the upper block segment 38a are formed with semi-circular grooves 42a and 42b for receiving the shaft 52 of the pressure applicator 50. When the bolt 44 is tightened, the middle and upper block segments 38a and 38b clamp onto the support bar 12, while the middle and lower block segments 38b and 38c simultaneously clamp around the shaft 52 of the pressure applicator 50.

As shown clearly in FIG. 2, the semi-circular grooves are arranged such that the pressure applicator 50 extends approximately 90° relative to the main support bar 12. Additional grooves may be provided to allow the pressure applicator 50 to extend at an angle relative to the main support bar 12. Other devices may also be used to clamp the main support bar 12 and the shaft 52 to one another.

The pressure applicator 50, shown in FIGS. 2 and 3, comprises a shaft 52 which is received between the middle and upper segments 38b and 38a of the mounting block 38. The shaft 52 is preferably made of a radiolucent material. An arcuate or generally C-shaped pressure plate 54 is secured at the outer end of the shaft 52, which may be constructed of aluminum. The use of aluminum, which is substantially radiolucent, allows a faint image of the pressure plate 54 to appear in the fluoroscopic image which is useful in correctly positioning the pressure applicator 50 along the support bar 12. It may also be made of a radiolucent material with a radiopaque marker embedded therein. The curvature of the pressure plate 54 allows the pressure plate 54 to contact the anterior side or front of the leg and either the medial or lateral surface of the leg. Thus, the pressure plate 54 can exert pressure both posteriorly and in the medial/lateral direction. Pressure in the posterior direction is controlled by sliding the pressure applicator 50 axially within the mounting block 38, generally perpendicular to the support bar 12. Pressure in the medial/lateral direction is provided by rotating the mounting block 38 about the axis of the main support bar 12.

FIG. 4 shows a second embodiment of a pressure applicator indicated generally at 50'. The pressure applicator 50' of the second embodiment is virtually the same as the first embodiment. The second embodiment differs in the shape of the pressure plate 54'. The pressure applicator 50' shown in FIG. 4 has a generally hook-shaped pressure plate 54' which extends around to the posterior surface of the limb. This pressure plate 50' can apply a force directed anteriorly as well as a force in the medial/lateral direction. An anterior force is applied by sliding the applicator 50' within the mounting block 38 along the axis of its shaft 52'. Force in the medial/lateral plane is applied by rotating the mounting block 38 about the main support bar 12.

Referring now to FIG. 5, there is an illustration showing how the apparatus of the present invention is used to distract a fracture of the femur. In this example, the patient is placed in a lateral decubitus position with the injured side up. A Kirschner wire is inserted under sterile conditions through the transcondylar region of the tibia. The segments of the main support bar 12 are assembled and the saddle 18 is inserted into the patient's groin. A Kirschner-type wire bow is applied to the Kirschner wire and then engaged with the hook 32 of the force applying unit 28. The bar clamp 22 is loosened to permit the support arm 20 to be adjusted. The support arm 20 is then slid manually along the support bar 12 until resistance against further movement is met. The support arm 20 is then secured in place on the main support bar 12 by tightening the bar clamp 22. After securing the support arm 20 in place on the main support bar 12, distraction of the ends of the bones can be achieved by turning the wing nut 34 on the force applying unit 28 clockwise. As the wing nut 34 is turned, the threaded rod 30 engaged with the Kirschner-type wire clamp is pulled back thereby applying a distally directed force to the patient's limb. As the wing nut 34 is tightened, the force is transferred through the main support bar 12, which is compressed, thereby urging the saddle 18 against the patient's groin. Engagement of the saddle 18 with the groin provides resistance against the traction force. The surgeon continues turning the wing nut 34 until the proper limb length is obtained.

Figure 7:
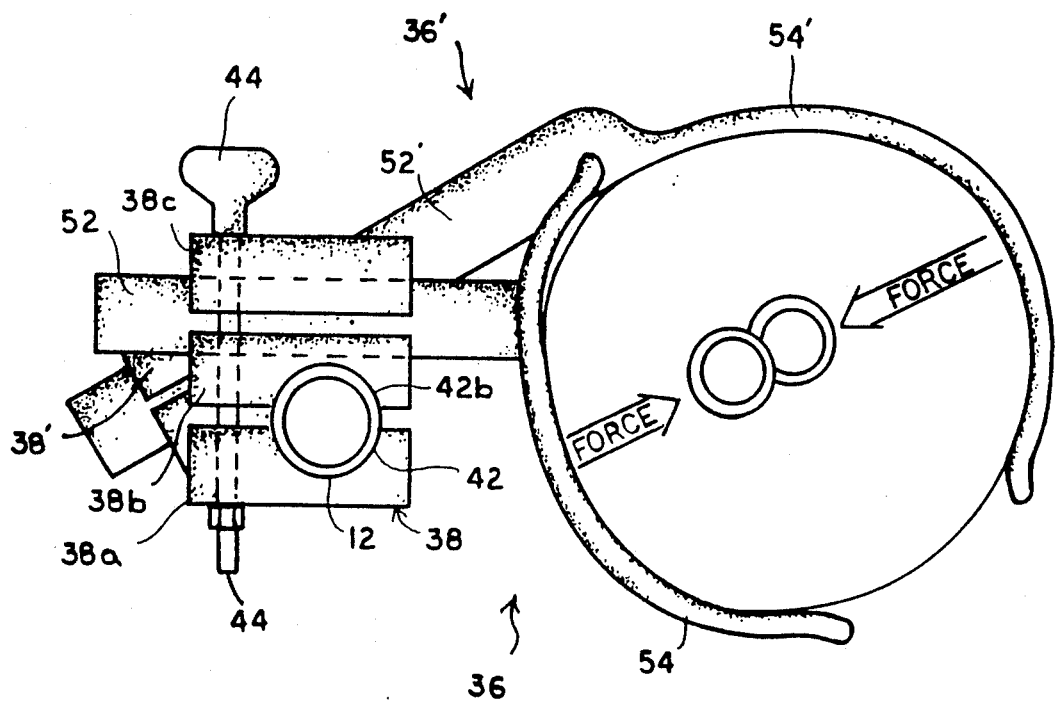
FIG. 7 is an elevational view illustrating how two reduction units are used to reduce a bone fracture.

In the event that there is displacement of the bone ends, it may be necessary to use the reduction unit 36 to correct the alignment of the ends. FIG. 6 shows the present invention being used to provide both distraction and reduction. In this case, traction is first applied to distract the ends of the bone as already described. After the correct limb length is obtained, the reduction unit 36 is mounted on the main support bar 22 and is used to apply force to the bone ends to correct any misalignment. FIG. 7 illustrates how two reduction units 36 and 36' may be used in conjunction, with one on the proximal fragment and one on the distal fragment, to correct misalignment of the bone fragments. One of the reduction units 36 is used to apply an outwardly and posteriorly directed force to one of the bone fragments. The other reduction unit 36' is used to provide an inwardly and anteriorly directed force to the other bone fragment. Once proper anatomical alignment of the bones has been obtained, the bone fragments can be fixed by means of an intramedullary nail.

Based on the foregoing, it is apparent that the present invention provides a relatively simple and easy method for distracting and reducing fractures of the long bones. Because the apparatus of the present invention is radiolucent, it will not interfere with fluoroscopic imaging. Further, it can be readily disassembled and placed in an autoclave for sterilization between uses. Because it is sterile, it can be adjusted by the surgeon.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. A surgical device for setting fractures of a patient's limb comprising:
   (a) a main support bar which extends generally parallel to the patient's fractured limb;
   (b) a saddle secured at one end of said main support bar for engagement with the person's groin or axilla;
   (c) force applying means mounted on the main support bar, wherein said force applying means is positionable with the patient's limb and in general alignment with the longitudinal axis of the patient's limb and engageable with a means for engaging the body for applying a distally directed force to the patient's limb through the body engaging means to distract the fracture wherein the saddle is pressed into the patient's groin or axilla upon application of the distally directed force to the patient's limb; and
   (d) a first reduction unit adjustably mounted along the main support bar for engaging the limb at the location of the fracture and at areas adjacent to the fracture for applying a tranversely directed force to align the bone fragments.

2. The surgical device of claim 1 further including a support arm slidably mounted on the main support bar, and wherein said force applying means is mounted on said support arm.

3. The surgical device of claim 1 wherein the reduction unit includes a mounting block mounted on the main support bar, and a pressure applicator movably mounted with respect to said mounting block for engaging and applying a corrective force to the fractured limb to realign the bone fragments.

4. The surgical device of claim 3 wherein the pressure applicator comprises a generally arcuate-shaped pressure plate.

5. The surgical device of claim 4 wherein said pressure plate is mounted at one end of a shaft, and wherein the pressure applicator slides axially back and forth along the axis of said shaft to produce an anteriorly or posteriorly directed pressure on the fractured limb.

6. The surgical device of claim 5 further including means for fixing the position of the pressure applicator once the proper degree of pressure is applied to the fractured limb.

7. The surgical device of claim 4 wherein the mounting block is rotatably mounted on said main support bar, and wherein said pressure plate is shaped to apply medially or laterally directed pressure to the fractured limb upon rotation of the pressure plate.

8. The surgical device of claim 1 wherein the force applying means includes screw adjustment means for applying the distally directed force to the patient's limb.

9. The surgical device of claim 1 further including a second reduction unit mounted on the support member wherein the first and second reduction units are useable in combination to apply pressure simultaneously on opposite sides of the fracture to correct displacement of the bone fragments.

10. The surgical device of claim 1 wherein the first and second reduction units are useable to apply pressure simultaneously on opposite sides of the fracture and in generally opposing directions so as to realign the fracture.

11. A surgical device for setting fractures of a patient's limb comprising:
   (a) a support member extending generally parallel to the patient's limb and having a first end and a second end;
   (b) a saddle connected to the first end of the support member and being fittable against the groin or axilla area of the patient;
   (c) a transverse member extending laterally from the support member, said transverse member being mounted for sliding movement along an intermediate portion of the support member between the first and second ends;
   (d) force applying means mounted on the transverse member, wherein the force applying means is positionable over the patient's limb and in general alignment with the longitudinal axis of the patient's limb; and
   (e) body engaging means for connecting the force applying means to the patient's limb, wherein the force applying means is adjustable to apply a distally directed force to the patient's limb through the body engaging means to distract the fracture, wherein as the fracture is distracted the saddle is pressed into the person's groin or axilla.

12. The surgical device according to claim 11 further including a first reduction unit slidably mounted along the main support bar for applying pressure to the limb at the location of the fracture to correct displacement of the bone fragments.

13. The surgical device of claim 12 wherein the reduction unit includes a mounting block mounted on the main support bar, and a pressure applicator movably mounted with respect to said mounting block for engaging and applying a corrective force to the fractured limb to realign the bone fragments.

14. The surgical device of claim 13 wherein the pressure applicator comprises a generally arcuate-shaped pressure plate.

15. The surgical device of claim 12 wherein said pressure plate is mounted at one end of shaft and wherein the pressure applicator slides axially back and forth along the axis of said shaft to produce a laterally directed pressure on the fractured limb.

16. The surgical device of claim 15 further including means for fixing the position of the pressure applicator once the proper degree of pressure is applied to the fractured limb.

17. The surgical device of claim 12 wherein the mounting block is rotatably mounted on said main support bar, and wherein said pressure plate is shaped to apply anteriorly or posteriorly directed pressure to the fractured limb upon rotation of the pressure plate.

18. The surgical device of claim 11 wherein the force applying means includes screw adjustment for applying the distally directed force to the patient's limb.

19. The surgical device of claim 12 further including a second reduction unit mounted on the support member wherein the first and second reduction units are useable in combination to apply pressure simultaneously on opposite sides of the fracture to correct displacement of the bone fragments.

20. The surgical device of claim 18 wherein the first and second reduction units are useable to apply pressure simultaneously on opposite sides of the fracture and in generally opposing directions so as to realign the fracture.

* * * * *